United States Patent [19]

Nishimura

[11] Patent Number: 4,822,765
[45] Date of Patent: Apr. 18, 1989

[54] PROCESS FOR TREATING ACTIVATED CARBON WITH AQUEOUS AMMONIA

[75] Inventor: Yasushi Nishimura, Tokyo, Japan

[73] Assignee: Kureha Kagaku Kogyo Kabushiki Kaisha, Tokyo, Japan

[21] Appl. No.: 47,291

[22] Filed: May 8, 1987

Related U.S. Application Data

[60] Division of Ser. No. 759,933, Jul. 29, 1985, Pat. No. 4,761,284, which is a continuation of Ser. No. 470,762, Feb. 28, 1983, abandoned, which is a continuation-in-part of Ser. No. 376,960, May 11, 1982, abandoned, which is a continuation-in-part of Ser. No. 274,736, Jun. 18, 1981, abandoned, which is a continuation-in-part of Ser. No. 158,203, Jun. 10, 1980, abandoned, which is a continuation-in-part of Ser. No. 52,141, Jun. 26, 1979, abandoned, which is a continuation-in-part of Ser. No. 970,106, Dec. 18, 1978, abandoned.

[30] Foreign Application Priority Data

Dec. 27, 1977 [JP] Japan ................. 52-156546
Jun. 26, 1979 [JP] Japan ................. 54-80537

[51] Int. Cl.$^4$ ............... C01B 31/08; C01B 31/02; B01J 20/20; A61K 33/44
[52] U.S. Cl. .................. 502/418; 423/460; 423/461; 424/125; 502/416
[58] Field of Search ............ 502/416, 418, 180, 26; 423/460, 461

[56] References Cited

U.S. PATENT DOCUMENTS

| 1,502,076 | 7/1924 | Weinrich | 502/26 |
| 1,542,006 | 6/1925 | Sauer | 424/125 |
| 2,143,088 | 1/1939 | Rockwell | 502/416 |
| 2,787,579 | 4/1957 | van der Weel | 167/82 |
| 3,917,806 | 11/1975 | Amagi et al. | 423/449 |
| 3,917,821 | 11/1975 | Manes | 424/125 |
| 4,169,051 | 9/1979 | Satoh et al. | 218/23 |
| 4,299,805 | 11/1981 | Wells | 423/321 R |
| 4,415,478 | 11/1983 | Suggitt et al. | 423/461 |

FOREIGN PATENT DOCUMENTS

| 966618 | 4/1975 | Canada . | |
| 2315483 | 6/1976 | France . | |
| 50-18879 | 2/1975 | Japan . | |
| 52-30800 | 3/1977 | Japan . | |
| 62-23439 | 1/1987 | Japan | 502/180 |
| 51388 | 7/1966 | Poland . | |
| 476321 | 6/1979 | Spain . | |
| 1383085 | 2/1975 | United Kingdom . | |
| 145871 | 12/1976 | United Kingdom . | |
| 1525420 | 9/1978 | United Kingdom . | |
| 2012257 | 7/1979 | United Kingdom . | |

OTHER PUBLICATIONS

Chemical Abstracts: vol. 48 (1954) 13338i–13339a, Streib et al.
English Translation of an Official Action of the Examiner of the Netherlands Patent Office.
The United States Pharmacopeia, Nineteenth Revision, Jul. 1, 1975, p. 75.
Streib et al., Chemical Abstracts, vol. 48, 1954, 13338i–1339a.
Chin et al., Chemical Abstracts, vol. 73, 1970, 54118v.
Balatre et al., Chemical Abstracts, vol. 76, 1972, 49893b.
Amagi et al., Chemical Abstracts, vol. 82, 1975, 142169d.

Primary Examiner—Paul E. Konopka
Attorney, Agent, or Firm—Wegner & Bretschneider

[57] ABSTRACT

Activated carbon, useful in a pharmaceutical composition for adsorbing exogenous or endogenous toxins from the gastrointestinal tract of a patient can be prepared by a process including a step of treating activated carbon with an aqueous ammonia solution to provide a resultant activated carbon having a pH of 6 to 8.

13 Claims, No Drawings

PROCESS FOR TREATING ACTIVATED CARBON WITH AQUEOUS AMMONIA

CROSS-REFERENCE TO RELATED APPLICATIONS

This application is a division of Ser. No. 759,933, filed July 29, 1985, now U.S. Pat. No. 4,761,284 which is a continuation of Ser. No. 470,762, filed Feb. 28, 1983 (now abandoned), which is a continuation-in-part of Ser. No. 376,960, filed May 11, 1982 (now abandoned), which is a continuation-in-part of Ser. No. 274,736, filed June 18, 1981 (now abandoned), which is a continuation-in-part of Ser. No. 158,203, filed June 10, 1980 (now abandoned), which is a continuation-in-part of Ser. No. 052,141, filed June 26, 1979 (now abandoned), which is a continuation-in-part of Ser. No. 970,106, filed Dec. 18, 1978 (now abandoned).

SUMMARY OF THE INVENTION

In a first aspect of the present invention, there is provided a pharmaceutical composition having an antidotal activity, which in dosage unit form is capable of adsorbing exogenous or endogenous toxins in the gastrointestinal tract of a patient without causing the patient to become constipated, comprising, as an active ingredient, spherical particles of activated carbon including at least 85% in number of microscopically spherical particles of activated carbon which have smooth and convex-curved surfaces without sharp edges, maximum to minimum diameter ratio of 1.0 to 1.3, diameters of 0.05 to 2.0 mm and pore cavity volume not more than 0.05 cc/g determined in the range of pore-radius of 5,000 to 75,000 Å.

In a second aspect of the present invention, there is provided a method of treating a patient suffering from exogenous or endogenous toxins in the gastrointestinal tract, comprising orally administering to the patient an antidotally effective amount of spherical particles of activated carbon in dosage unit form capable of adsorbing the toxins in the gastrointestinal tract of the patient without disintegration of the spherical particles of activated carbon and without causing the patient to become constipated. The spherical particles of activated carbon including at least 85% in number of microscopically spherical particles of activated carbon having smooth and convex-curved surfaces without sharp edges, maximum to minimum diameter ratios of 1.0 to 1.3, diameters of 0.05 to 2.0 mm and pore cavity volume not more than 0.05 cc/g determined in the range of pore-radius of 5,000 to 75,000 Å.

In a third aspect of the present invention, there is provided an antidote in dosage unit form which consists of spherical particles of activated carbon comprising at least 85% in number of microscopically spherical particles of activated carbon having a pH of 6 to 8, which is useful in antidotally removing poisonous or harmful substances from the gastrointestinal tract. More particularly, it relates to an antidote of spherical particles of activated carbon comprising at least 85% in number of microscopically spherical particles of activated carbon having a pH of 6 to 8, which does not show any side effect of causing constipation, as will be frequently experienced in prior art counterparts, when applied for counteracting poisonous substances existing or formed in the gastrointestinal tract.

DETAILED DESCRIPTION OF THE INVENTION

The invention relates to an antidote which consists of spherical particles of an activated carbon including at least 85% in number of microscopically spherical particles of activated carbon, and is useful in removing poisonous or harmful substances from the gastrointestinal tracts. More particularly, it relates to a dosage unit form antidote of spherical particles of an activated carbon including at least 85% in number of microscopically spherical particles of activated carbon which have smooth and convex-curved surfaces without sharp edges, maximum to minimum diameter ratios of 1.0 to 1.3, diameters of 0.05 to 2.0 mm and pore cavity volume not more than 0.05 cc/g determined in the range of pore-radius of 5,000 to 75,000 Å. The antidote does not show any side effect of causing constipation, as is frequently experienced with prior art counterparts when applied for counteracting poisonous substances existing or formed in the gastrointestinal tracts.

It is known in the prior art that oral administration of activated carbon is an effective remedy for intestinal troubles. It has been reported that orally administered activated carbon shows an excellent therapeutical efficacy particularly on bacterial-infectious diseases such as dysentery, cholera, typhoid abdominalis, alimentary intoxication, indigestion, flatus in intestines, chronic gastritis, epilepsy, dizziness, chlorosis, anthrax and the like. In cases of undesirable intake of drugs and poisons, the oral administration of activated carbon results in first-aid activity. Furthermore, oral use of activated carbon is effective for removing noxious substances from the gastrointestinal tracts which form due to abnormalities in metabolism caused by various diseases. These effects are considered to be due to the fact that toxins, abnormal metabolites or substances which induce the formation of such toxins and/or abnormal metabolites in the gastrointestinal tracts are adsorbed on the activated carbon. The activated carbon is completely harmless to living bodies and when orally administered to the living body, it is discharged outside of the body bearing thereon the noxious substances.

Previously, activated carbon used for its detoxicative function has been in the form of fine powder, and it was orally administered with water or was taken after formulating into tablets. The activated carbon ingested as tablets is disintegrated to a powdery state in the digestive tracts and then exhibits its adsorbency as in the case of ingesting powdery activated carbon with water. However, the use of activated carbon as an antidote by ingestion of powdery activated carbon or its tablets causes the serious side effect of constipation. Particularly, since activated carbon is administered to patients with various diseases where the patient's physical strength is low, the constipation side effect not only gives pain to the patient but also may cause a fatal situation unless the feces are removed by mechanical means. In order to solve those problems, purgatives or laxatives may be used in some cases. However, the following additional problems in therapy arise from use of purgatives or laxatives:

(1) where purgatives are used together with activated carbon, the adsorbing or detoxicating function of activated carbon is impeded by action of purgatives;

(2) where the purgatives are administered at the time of constipation, it is fairly difficult to control the patient's condition without either some constipation or diarrhea, even if dosage and administration timing or the purgatives are critically adjusted;

(3) where the administration of activated carbon is repeated over relatively long periods, unavoidable problems arise in that the patient's physical stamina is depleted as a result of recurrent symptoms of diarrhea which leads to malabsorption of the nutrients from intestine.

Accordingly, a highly antidotally effective activated carbon which does not cause constipation after its ingestion has been strongly desired.

It has now been found that spherical particles of activated carbon, preferably at a pH of 6 to 8, comprising at least 85%, preferably 90%, in number of microscopically spherical particles of activated carbon which have smooth and convex-curved surfaces without sharp edges, a maximum to the minimum diameter ratio of 1.0 to 1.3, diameters of 0.05 to 2.0 mm and a pore cavity volume not more than 0.05 cc/g determined in the range of pore-radius of 5,000 to 75,000 Å, do not exhibit the secondary effect of causing constipation but show excellent antidotal activity.

The antidote according to the present invention is administered in dosage unit form, and is composed of spherical particles of activated carbon containing at least 85% in number of microscopically spherical particles of activated carbon which have a smooth, convex-curved surface without edges, maximum to minimum diameter ratios of 1.0 to 1.3, both the essentially spherical particles and the microscopically spherical particles of activated carbon have a diameter of 0.05 to 2.0 mm, preferably 0.1 to 1.0 mm, surface area of 500 to 2,000 m$^2$/g, pore cavity volume of not more than 0.05 cc/g determined in the range of pore-radius of 5,000 to 75,000 Å and 0.05 to 1.0 cc/g, preferably 0.1 to 0.8 cc/g, in pore cavity volume as determined in the range of pore-radius of 100 to 75,000 Å. The spherical particles of activated carbon with a diameter smaller than 0.05 mm are not satisfactory with respect to the secondary effect of causing constipation although they do show an antidotal activity. With the sizes larger than 2.0 mm, not only are the spheres hard to administer orally, but also the intended level of antidotal efficacy cannot be developed quickly.

The shape of the activated carbon particles is one of the important factors in attaining the satisfactory medical efficacy of the present invention and it is necessary that the particles be essentially spherical, and further, it is necessary that the essentially spherical particles of activated carbon comprise at least 85% in number of microscopically spherical particles of activated carbon, both particles of activated carbon having the above-mentioned parameters. Also, the surface area and the pore cavity volume are the important factors in the simultaneous development of a satisfactory antidotal efficacy and the suppression of the secondary effect of causing constipation.

If the pore cavity volume of the spherical particles of activated carbon determined in the range of pore-radius of 5,000 to 75,000 Å, is larger than 0.05 cc/g, coagulation of the feces within the digestive tract is shown to occur; accordingly, constipation is experienced and the particles remove the digestive enzymes within the digestive tract by adsorption and excretion of the particles. In addition, spherical particles of activated cargon with large pore cavity volume in the range of pore-radius become pulverized because of their poor strength due to their coarseness.

Consequently, it is necessary that the pore cavity volume of the spherical particles of activated carbon, determined in the range of pore-radius of 5,000 to 75,000 Å, be as small as possible, and it is preferably no greater than 0.05 cc/g.

Also if the surface area and the pore cavity volume, determined in the range of pore-radius of 100 to 75,000 Å, are too small, the adsorbing activity becomes so small that satisfactory levels of the antidotal efficacy can not be obtained. On the contrary, when the surface area and the pore cavity volume, determined in the range of pore-radius of 100 to 75,000 Å, are larger than 1.0 cc/g, the constipation tends to undesirably result although the antidotal activity is developed. It is considered that the microscopically spherical activated carbon of such larger surface area and pore cavity volume, determined in the range of pore-radius of 100 to 75,000 Å, are lower in physical strength, so that it will readily be broken to pieces during or after the internal administration, causing the side effect of constipation.

According to the present invention, the surface area of both the essentially spherical particles and the microscopically spherical particles of activated carbon is in the range of 500 to 2,000 m$^2$/g, preferably 700 to 1,500 m$^2$/g, as determined by a commercially available surface area-determining instrument. The pore cavity volume is determined by a commercially available mercury porosimeter and is in the range of 0.05 to 1.0 cc/g, preferably 0.1 to 0.8 cc/g, with pore-radius of 100 to 75,000 Å.

The followings are the explanation of the method for producing the spherical particles of activated carbon according to the present invention.

The method of producing the spherical particles of activated carbon according to the present invention comprises formulating the starting material into minute spherical particles and activating the formulated minute particles to be minute spherical particles of activated carbon.

The known starting materials for producing the particles of the activated carbon having the characteristic properties include sawdust, coal, coconut-shell, pitch, organic synthetic polymer and the like. These materials can be converted into spherical particles of activated carbon.

In cases where sawdust, coal and coconut-shell, etc. are used as the raw material, the pulverized material is formulated into minute spherical particles by the use of a binder, for instance, pitch, and then the particles are carbonized in an inert atmosphere at a temperature of 800° to 1,000° C. The carbonized particles are activated by heating at a temperature of 900° to 1,000° C. in an atmosphere of water vapor. Where a pitch is used as the raw material, the pitch is formulated into minute spherical particles in a molten state according to the conventional method (i.e., which method disclosed in Japanese Patent Publication No. 50-18879), said method comprises shaping molten pitch into small-sized spheres, oxidizing the spheres to render them infusible, heating and baking the spheres for carbonization in an inert atmosphere at a temperature of 800° to 1,000° C., and activating at a temperature of 900° to 1,000° C.

By using a pitch as the raw material, the ratio of truly spherical particles in the thus obtained minute spherical particles of activated carbon is much improved, and the surface of the particles becomes much smoother with an improved mechanical strength. Accordingly, as the method for producing the activated carbon for use in the antidote of the present invention, it is particularly preferable to adopt the latter method of production.

In the production, the thus obtained spherical particles of activated carbon are sifted to a size suitable for internal administration. Since the sifting is carried out in order that the size of spherical particles of activated carbon is suitable for internal administration, the size uniformity of each particle is improved and the diameter ratio of the largest particles to the smallest particle is 1.0 to 3.0.

In the case where the spherical particles of activated carbon according to the invention are applied as an antidote, it is preferable to adopt the same method of ingestion as that for ingesting "charcoal for medical use." It is most convenient to ingest the spherical particles of activated carbon after dispersing into drinking water to create a pharmaceutically acceptable aqueous slurry.

A pharmaceutical composition in the form of tablets, granules and capsules is possible for administration orally, said composition comprising spherical particles of activated carbon and a pharmaceutical carrier, such as water-soluble or swellable high polymeric substances which dissolve or swell in water or aluminum hydroxide gel which releases the combined particles of activated carbon into free original spherical particulate state after ingestion.

Water-soluble high polymeric substances which dissolve or swell in water include: soluble starch, dextrin, gelatin, gluten, gum arabic, methylcellulose, ethylcellulose, carboxymethylcellulose or its salt, hydroxyethylcellulose, hydroxypropylmethylcellulose, crystalline cellulose, α-cellulose, amylose, polyvinyl alcohol, polyvinyl acetate, polyethylene glycol, etc.

The weight ratio of the activated carbon to the pharmaceutical carrier in the composition is in a range of 100:0 to 50:50.

The dosage level of the spherical particles of activated carbon is usually 0.5 to 10 g/60 kg of body weight three to five times per day, however, it depends on the degree of disease, the necessity of urgent detoxication, etc. Although it is preferable to ingest after or between meals, the ingestion can be at anytime when necessary in urgent cases.

It has not been previously expected that essentially spherical particles of activated carbon as specified above would not cause any constipation when administered while still exhibiting the antidotal efficacy. Although the reason has not been elucidated, it is presumably because the spherical particles of activated carbon of the present invention retain their adsorbency of exogenous and endogenous toxins even in the presence of substances such as ingested foods, digested foods, feces and bile acids better than the conventional powdery activated carbon or simply formulated particles or granules from powdery activated carbon.

Presumably the conventional powdery active carbon or formulated particles or granules of activated carbon collapse into original powdery carbon in the juices of alimentary canal and tend to adsorb the stimulants for intestines thus weakening the entero-cinesia. At the same time, said particles are well mixed with feces, resulting in an increase of cohesion of the feces and constipation. In contrast, the spherical particles of activated carbon according to the invention do not increase the cohesion of the feces due to smoothness of the particles' essentially spherical surfaces and lower adsorption of the stimulants for the intestines. Also, the spherical particles of the invention give proper stimulation to the intestines, thus they do not cause constipation.

In a further aspect, there is provided a method of producing the spherical particles of activated carbon according to the invention which are prepared from heavy hydrocarbons, i.e. pitch, by the following processes.

The pitch is formulated in a melt state into small spherical particles and after cooling they are oxidized, infusibilized and then carbonized at a temperature of 800° to 1,000° C. in an inert atmosphere. Finally, they are activated at a temperature of 900° to 1,000° C. in an atmosphere of water vapor to be minute spherical particles of activated carbon 0.05 to 2 mm in diameter, 500 to 2,000 $m^2/g$ in specific surface area, 0.05 to 1.0 ml/g in pre volume of pores 100–75,000 in pore-radius, pH of the particles being 8 to 10 (alkaline).

In another process, the thus obtained particles are further treated by bringing them into contact with a dilute aqueous ammoniacal solution containing 1 to 1,000 ppm, preferably 5 to 100 ppm, of $NH_3$ and dried. The product have the same size, the same specific surface area and the same pore volume as the particles of activated carbon before the ammoniacal treatment, but the pH of particles of the final product is 6 to 8 (acidic).

The starting materials for producing the spherical particles of activated carbon having the above-mentioned characteristic properties are known ones including coal, pitch, organic synthetic polymer and the like. These materials can be converted into spherical particles of activated carbon.

For example, the spherical particles of activated carbon are made by a process which comprises the steps of shaping an above-mentioned powdery material into small-sized spheres by the use of a binder such as pitch, heating and baking for carbonizing the thus formed spheres by heating and baking in an inert atmosphere at a temperature of 800°–1,000° C., and activating them in an atmosphere of steam at a temperature of 900°–1,000° C. Alternatively, there is known a process as described in, for example, Japanese Patent Publication No. 50-18879, where said process comprises shaping a pitch in a molten state into small-sized spheres, oxidizing the spheres to render them infusible, heating and baking the spheres for carbonization in an inert atmosphere at a temperature of 800°–1,000° C., and activating at a temperature of 900°–1,000° C. The latter process is especially suitable for the production of spherical particles of activated carbon according to the present invention since it can yield spherical particles of activated carbon having higher sphericity, higher physical strength and smoother surfaces.

The second process of the preparation of the spherical particles of activated carbon of the invention is particularly important because the pH of the particles was changed in this stage from 8–10 to 6–8. The ammoniacal treatment conditions depend upon the stage of particles of carbon activated by water vapor treatment. However, usually the concentration of $NH_3$ in the aqueous ammoniacal solution is 1 to 1,000 ppm, preferably 5 to 100 ppm; the volume ratio of the aqueous ammonical solution to the particles of activated carbon is 1 to 50, preferably 2 to 10, and the temperature is maintained at 10° to 50° C. for 0.5 to 5 hours. Too much ammonia in the solution makes the pH of the product too high and too little ammonia retains the alkaline pH of the product.

The reason why the originally alkaline particles were changed by an alkaline reagent, an aqueous ammoniacal solution, to the acidic-neutral particles has not yet been elucidated, and the above-mentioned change is quite unexpected.

The thus treated particles of activated carbon are usually dried at a temperature of 100° to 150° C., and sifted to a size suitable for oral administration. It is preferable to prepare a uniformly sized product, that is, the narrower the size distribution, the better. Accordingly, the sifting is carried out to obtain the product having the interparticles size ratio of the largest particle to the smallest particle of within 1.0 to 3.0. Of course, the sifting may be carried out before the treatment by the ammoniacal solution.

The present invention is explained in more detail in the following Examples; however, it should be recognized that the scope of the present invention is not restricted to these Examples.

Example I

Seven hundred and fifty parts by weight of a pitch (with a softening point of 190° C., a content of nitrobenzene-insoluble matter of 30% by weight, and H/C atomic ratio of 0.6) obtained by thermal cracking of a crude oil and 250 parts by weight of naphthalene were placed in a stainless steel-autoclave equipped with an agitator, and they were mixed for dissolution at 170° C. To the thus formed solution were added 3,000 parts by weight of a 0.5% aqueous solution of "Gosenol GH0-17" (polyvinyl alcohol-based suspending agent, product of Nippon Synthetic Chemical Industry Co., Ltd.), followed by violently agitating at 140° C. for 3 minutes and then cooling to room temperature still under agitation to obtain spherical particles of pitch. After removing most of water of the solution by filtration, the particles were immersed in methanol in an amount of 5 time by weight as large as that of the particles and the thus formed slurry was shaken to remove naphthalene by dissolution in methanol. After air-drying, the particles were heated in a small-sized rotary kiln up to 300° C. at a heating rate of 25° C./hr while passing air therein thereby obtaining infusible, spherical particles. Then the passage of air was stopped and the temperature of the kiln was raised up to 900° C. for carbonization while feeding steam to the particles in the kiln. The kiln temperature was maintained at 900° C. so as to make the activation proceed. As a result, there were obtained the spherical particles of activated carbon of high sphericity, having a diameter of 0.07 to 1.8 mm.

Three specimens of the spherical particles of activated carbon indicated in Table 1 were those obtained by sifting the products of the process.

TABLE 1

| Characteristic Properties of Spherical Particles of Activated Carbon | | | |
|---|---|---|---|
| Characteristic Properties | Specimen 1 (particle size: 0.07–0.25 mm) | Specimen 2 (particle size: 0.25–0.6 mm) | Specimen 3 (particle size: 0.6–1.2 mm) |
| Surface area (m²/g) | 750 | 1600 | 1300 |
| Volume of pore cavity (cc/g) *1(determined in the range of pore-radius of 100 to 75,000Å | 0.12 | 0.38 | 0.27 |
| Volume of pore cavity (cc/g) *1(determined in the range of pore-radius of 5,000 to 75,000Å | 0.009 | 0.019 | 0.013 |
| Adsorbency (mg/g)*2 | | | |
| to indole | 340 | 570 | 455 |
| to octopamine | 120 | 210 | 150 |
| to phenylethanolamine | 185 | 380 | 290 |
| to phenylalanine | 150 | 250 | 195 |
| to tryptophane | 200 | 340 | 250 |
| Ratio of number of microscopically spherical particles to total number of particles (%)*3 | 95 | 99 | 97 |

Notes:
*1Determined by the mercury porosimeter (Porosimetro Model 70, product of Carlo Erba Co., Ltd., Italy).
*2Amount of adsorption determined by the use of an aqueous solution having a concentration of 20 mg/dl and adjusted in pH of 7.4 by means of a sodium potassium phosphate buffer solution.
*3Microscopically spherical particles of activated carbon designates particles having smooth and convex-curved surfaces without edges and ratios of the maximum diameter to the minimum diameter of 1.0 to 1.3.

The adsorptive ability of the spcimens were determined with regard to the amines such as indole and octopamine and abnormally accumulating amino acids in the gastrointestinal tracts which are presumed to be generated in the body due to the abnormal metabolish induced by hepatic diseases. It will be appreciated that all of the specimens passed the standard test such as purity test, weight loss on drying, and residue on ignition of "Medicinal Carbon" prescribed in the Pharmacopeia of Japan (the ninth revision).

Example 2

Seven hundred and fifty parts by weight of a pitch (with a softening point of 175° C., a content of nitrobenzene-insoluble matter of 25% by weight, and H/C atomic ratio of 0.63), obtained by thermal cracking of a crude oil and 250 parts by weight of naphthalene, were placed in a stainless-steel autoclave equipped with an agitator and they were mixed for dissolution at 170° C. To the thus formed solution were added 3,000 parts by weight of a 0.5% aqueous solution of "Gosenol GH-17" (polyvinyl alcohol-based suspending agent, product of Nippon Synthetic Chemical Industry Co., Ltd.), followed by violently agitating at 130° C. for 60 minutes and then cooling to room temperature still under agitation to obtain particles of pitch. After removing most of water of the solution by filtration, the particles were immersed in methanol in an amount of 5 time by weight as large as that of the particles and the thus formed slurry was shaken to remove naphthalene by dissolution in methanol. After air-drying, the particles were heated in a small-sized rotary kiln up to 300° C. at a heating rate of 25° C./hr while passing air therein, to obtain infusible spherical particles. Then the passage of air was stopped and the temperature of the kiln was raised to 900° C. for carbonization while feeding steam to the particles in the kiln. The kiln temperature was maintained at 900° C. so as to make the activation proceed. The heat-treated particles were sifted to be in a size of 0.1 to 1.5 mm. As a result, the spherical particles of activated carbon of high sphericity were obtained. Two kinds of products, different in the degree of activation, were prepared by changing the time period of activation. Sample No. 1 was taken from the product with lower degree of activation and sifted to be in a range of particle size and Sample No. 2 was taken from the product with higher degree of activation and also sifted to be in a range of particle size. Then, the two kinds of particles of activated carbon were immersed into an aqueous ammoniacal solution containing 10 ppm of $NH_3$ in a volume/weight ratio of the aqueous solution to the particles of activated carbon of 10 ml/1 g at the room temperature for 3 hours, then separated from the solution and dried at a temperature of 110° C. for 16 hours to obtain two products. Those prepared from the activated carbon with lower degree of activation were named Sample No. 1-1 and those prepared from the activated carbon with higher degree of activation were name Sample No. 2-1. The characteristic properties of these four kinds of samples are shown in Table 2.

Further, the particles adsorbing activity was evaluated by an in vitro test where in their adsorbing activity for creatinine and ureic acid was determined, the two above-mentioned compounds are known as representative noxious products produced in vivo in the case of the renal failure and accumulate in the alimentary canal.

TABLE 2

Characteristic Properties of Spherical Particles of Activated Carbon

| Characteristic Properties | Sample No. 1-1 | Sample No. 1 | Sample No. 2-1 | Sample No. 2 |
|---|---|---|---|---|
| Particle size (mm.) | 0.21–0.35 | 0.21–0.35 | 0.25–0.6 | 0.25–0.6 |
| Specific surface area ($m^2/g$) | 830 | 830 | 1500 | 1500 |
| Specific volume of pore (ml/g)*[1] | 0.15 | 0.15 | 0.35 | 0.35 |
| Absorbing activity (mg/g)*[2] | | | | |
| Creatinine | 51 | 41 | 63 | 52 |
| Uric acid | 110 | 98 | 145 | 120 |
| pH*[3] | 6.1 | 8.2 | 7.2 | 8.9 |

Notes
*[1]Determined by the mercury porosimeter (Porosimetro Model 70, product of Carlo Erba Co., Ltd., Italy).
*[2]Determined in phosphate buffer solution at pH of 7.4 with a concentration of 5 mg/dl of substrate.
*[3]The pH of particles of activated carbon is determined by the method indicated in Japanese Pharmacopoeia 9th Rev. (Pharmacological Charcoal).
Three grams of the Sample is immersed in 60 ml of distilled water and the mixture is boiled for 5 minutes, and after cooling, an amount of distilled water is added to the mixture to recover the evaporation loss and after filtering the mixture the pH of the aqueous phase is determined. The value is adopted to be the pH of the sample.

In addition, it will be appreciated that all of the samples passed the standard test such as the identification test, purity test, weight loss on drying, and residue on ignition of "Medicinal Carbon" prescribed in the Pharmacopoeia of Japan (the ninth revision).

Acute Toxicity Test

The test was conducted on the mice using the specimens indicated in Table 1. The test results are shown below, from which it was confirmed that the spherical particles of activated carbon according to the invention were very high in safety even though administered in large doses.

For the test, the commercially available mice of ICR-JCL strain (weighing 22±1 g) were used and the particles of activated carbons of Specimens 1 and 3 of Table 1 were used as they are, but that of Specimen 2 was finely ground. These specimens were forcibly p.o. administered by a stomach tube. One week after the administration, the mortality of the mice was observed and $LD_{50}$ was determined by the Litchfield-Wilcoxon's method. The results are shown in Table 3.

One week after the administration, the mice were sacrificed and an autopsy performed, but no specific abnormal findings were observed in appearance and the internal organs showed no toxic symptoms involved.

TABLE 3

| | Acute Toxicity Test | | |
|---|---|---|---|
| Specimen | Route | Number of Mice | $LD_{50}$ (mg/kg) |
| Specimen 1 | Oral Administration | 10 | >15,000* |
| Specimen 2 | Oral Administration | 10 | >15,000* |
| Specimen 3 | Oral Administration | 10 | >15,000* |

*The dosage more than 15,000 mg/kg was found to be experimentally very difficult and so the administration test was stopped at the maximum dosage of 15,000 mg/kg. No case of death was observed at the highest dosage of of 15,000 mg/kg.

Example 3

(Antidotal Test)

Groups of rats of Wistar strain, weighting 130 to 140 g, were used and orally administered with 20 mg/kg of pentobarbital sodium as an aqueous solution. Immediately after the administration, the specimens of Table 1 and the medicinal powdery carbon were respectively suspended in water, each of which was orally administered at the dosage of 200 mg/kg to each 10 animals of the test group. For reference, a comparative test was simultaneously carried out without the administration of any activated carbon. Then, the ratio of an average value of the maximum concentration of pentobarbital sodium in the blood of the rats in each group to that of animals in the comparative test group was calculated as a removal rate, with the results shown in Table 4.

TABLE 4

| Antidotal Effect of Specimens of Activated Carbon | | | | |
|---|---|---|---|---|
| Activated Carbon Sample | Specimen 1 | Specimen 2 | Specimen 3 | Medicinal Powdery Carbon |
| Removal Rate (%) | 88.5 | 96.3 | 93.1 | 92.2 |

Ninety minutes after the administration of the activated carbon, the test rats were each anesthetically sacrificed and their digestive tracts were removed to observe the degree of intra-intestinal transfer of the carbon. That is, the ratio of a transferred distance of the activated carbon to the overall length of from the cardia to the end of rectum was determined as a transfer rate. As will be apparent from the results shown in Table 5, the specimens of activated carbon of the invention indicated in Table 5, the specimens of activated carbon of the invention indicated in Table 1 are significantly greater in the transfer rate, it is thus hard to cause constipation as compared with the known powdery carbon.

TABLE 5

| Intestinal Transfer Rate of Specimens of Activated Carbon | | | | |
|---|---|---|---|---|
| Activated Carbon Sample | Specimen 1 | Specimen 2 | Specimen 3 | Medicinal Powdery Carbon |
| Removal Rate (%) | 69.6 | 71.4 | 72.5 | 55.5 |

Example 4

Groups of rats of Wistar strain, weighting 130–140 g, were used and orally administered with 20 mg/kg of pentobarbital sodium as an aqueous solution. Immediately after the administration, the samples of Table 2 were respectively suspended in water, each of which was orally administered at the dosage of 200 mg/kg to each 10 animals of the test group. For reference, a comparative test was simultaneously carried out without the administration of any activated carbon. Then, the ratio of an average value of the maximum concentration of pentobarbital sodium in the blood of the rats in each group to that of animals in the comparative test group was calculated as a rate of removal, with the results shown in Table 6.

As is seen in Table 6, high antidotal effect is observed in every sample, however, the effect is especially high in Samples No. 1-1 and No. 2-1 (those treated with $NH_3$) and Samples No. 1 and No. 2 (those not treated with $NH_3$).

TABLE 6
Antidotal Effect of Samples of Activated Carbon

| Sample | Sample No. 1-1 | Sample No. 1 | Sample No. 2-1 | Sample No. 2 |
|---|---|---|---|---|
| Rate of Removal (%) | 92.0 | 88.0 | 98.5 | 95.0 |

Ninety minutes after the administration of the activated carbon, the test rats were each anesthetically sacrificed and their digestive tracts were removed to observe the degree of intra-intestinal transfer of the carbon. That is, the ratio of a transferred distance of the activated carbon to the overall length of from the cardia to the end of rectum was determined as a transfer rate. As will be apparent from the results shown in Table 7, the samples of activated carbon of the invention are significantly greater in the rate of transfer, it is thus hard to cause constipation as compared with the known powdery carbon.

TABLE 7
Intestinal Rate of Transfer Of Samples of Activated Carbon

| Sample | Sample No. 1-1 | Sample No. 1 | Sample No. 2-1 | Sample No. 2 |
|---|---|---|---|---|
| Rate of Transfer (%) | 72.0 | 68.2 | 75.5 | 72.0 |

Example 5

The ratio of the diameter of the largest particles to that of the smallest particle was adjusted to 1 to 3 by sifting the spherical particles of activated carbon produced by the same method of Example 1, of 0.1 to 1.5 mm in diameter containing truly spherical particles in a high extent.

The properties of the thus obtained spherical particles of activated carbon are shown in Table 8, and those of the conventional powder of activated carbon and the granulated particle of activated carbon produced by the following method are also shown as Comparative specimens in Table 8.

A gel-like precipitate was obtained by mixing the 1 molar aqueous solution of sodium metasilicate into the 1 molar aqueous solution of sodium aluminate at a temperature of about 50° C. After separating the thus obtained precipitate by centrifugation and washing sufficiently well with water, the precipitate was added to a 2 molar aqueous solution of magnesium chloride and well mixed. After separating the precipitate, the treatment with magnesium chloride solution was repeated. After separating the thus precipitated product by centrifugation and washing the precipitate with water throughly, a gel-like precipitate of aluminum magnesium silicate was obtained.

In the next step, 170 g of powder activated carbon was mixed with 32 g of the above-mentioned gel-like precipitate of aluminum magnesium silicate suspended in water and the mixture was formulated to granular form under stirring and adjusting tackiness of the mixture by water addition and then dried at a temperature of 60° C. overnight to be granulated carbon.

In Table 8, the adsorbencies of both spherical particles of activated carbon to creatinine is illustrated, creatinine being known as accumulating noxious substances formed in the living body in metabolic abnormality caused by renal diseases.

TABLE 8
Specific Properties of Activated Carbon

| Property | Specimen According to the Invention | Comparative Specimen (powdery charcoal) | Comparative Specimen (granulated particle) |
|---|---|---|---|
| Diameter (mm) | 0.25 to 0.6 | <0.06 | 0.1 to 0.6 |
| Specific surface area (m$^2$/g) | 1500 | 950 | 850 |
| Pore-volume ml/g*[1] | 0.35 | 1.8 | 1.7 |
| Pore-volume ml/g*[2] | 0.012 | 0.52 | 0.38 |
| Adsorbency (mg/g) to creatinine*[3] | 52 | 45 | 38 |

Notes
*[1] Pore-volume of pores having radius of 100 to 75,000Å, determined by "Porosimetro Model 70" made by Carlo Erba.
*[2] Pore-volume of pores having radius of 5,000 to 75,000Å, determined by "Porosimetro Model 70" made by Carlo Erba.
*[3] Adsorbency was determined in a phosphate buffer solution containing substrate at a concentration of 5 mg/dl at pH of 7.4.

The results of determination of the adsorbencies of the specimens to various digestive enzymes in vitro are shown in Table 9. In addition, the adsorbency of a commercial powdery charcoal to the same digestive enzymes are also shown in Table 9. The values of Table 9 are the determined value expressed by mg/g obtained by determination on each enzyme as a substrate at a concentration of 1 mg/dl in a phosphate buffer solution at pH of 7.4.

TABLE 9
Adsorbencies to Digestive Enzymes

| Enzyme | Specimen according to this invention | Powdery Charcoal |
|---|---|---|
| Pepsin | 12 | 85 |
| Chymotrypsin | 11 | 65 |
| Amylase | smaller than 1 | 5 |
| Lipase | 7 | 35 |

It is recognizable from Table 9 that the digestive enzyme adsorbency of the spherical particles of activated carbon according to the invention are generally lower than those of powdery charcoal and of granulated particles.

Example 6

(Adsorbing Activity)

In order to evaluate the actual adsorbing activity of the spherical particles of activated carbon of the present invention in the intestines, the following experiment was carried out in the presence of sodium stearate which hinders the adsorption of noxious substance by activated carbon in the intestines.

Sodium stearate was well dispersed in a phosphate buffer solution of pH 7.4 at a concentration of 2%, which is the estimated concentration of sodium stearate in the intestines, and creatinine was dissolved in the above-mentioned solution at a concentration of 15 mg/dl. Then the samples of Table 2 were respectively added to the above-mentioned solution and after 3 hours of shaking, each 5 ml of the mixture was collected. After adding 3 drops of an aqueous 10% solution of aluminum sulfate to the mixture to precipitate the stearic acid, the concentration of creatinine in the supernatant was determined by colorimetry. Except the colorimetry, all the procedures were carried at a temperature of 37° C.

The results of determination are shown in Table 10. As is seen in Table 10, the spherical particles of activated carbon of the invention showed conspicuously higher adsorptive activity than that of Samples (not treated by $NH_3$).

The results show that the spherical particles of activated carbon of the invention have a conspicuously improved activity in adsorbing noxious substances such as creatinine in the intestines even in the presence of substances such as sodium stearate, which hinder the adsorption of noxious substances by activated carbon in the intestines.

TABLE 10

| | Adsorption of Creatinine by Activated Carbon In the Presence of Sodium Stearate | | | |
|---|---|---|---|---|
| Sample | Sample No. 1-1 | Sample No. 1 | Sample No. 2-1 | Sample No. 2 |
| Amount adsorbed (mg/g)* | 12 | 5.2 | 18 | 7.8 |

Note
*mg of creatinine adsorbed on gram of sample.

Example 7

An aqueous solution of pentobarbital sodium was orally administered to groups of female Wistar rats of individual body weight of 130 to 140 g at a dose rate of 20 mg of the medicine per kg body weight. Immediately thereafter, an aqueous suspension of each specimen shown in Table 8 was orally administered at a dose rate of 200 mg/kg body weight. A group of the rats was kept as the control by administering only pentobarbital sodium. The number of rats in a group was 10. After pre-determined time periods, blood specimens were collected and the concentrations of pentobarbital sodium in the blood specimen were determined to find the mean value of the maximum concentration of the medicine in the blood. The percentage of the mean of maximum concentrations of the treated group to the mean of maximum concentrations of the control group is shown in Table 11 as the rate of removal of pentobarbital sodium from the rats.

As is seen in Table 11, the effect of removal of the medicine (referred to the effect of detoxication) was observed on every specimen of activated carbon, however, the specimen according to the invention showed a particularly remarkable detoxifying effect as compared to comparative specimens.

TABLE 11

| | Rate of Removal of Pentobarbital Sodium by Specimens | | |
|---|---|---|---|
| Property | Specimen According to the Invention | Comparative Specimen (powdery charcoal) | Comparative Specimen (granulated particle) |
| Rate of removal | 95.0 | 89.9 | 79.8 |

After 90 minutes of the administration of each specimen, all the animals were sacrificed by anesthesia and their digestive tracts were removed to observe the intestinal transfer of the administered activated carbon. The ratio (percentage) of the distance from the cardia to the point at which the activated carbon have arrived to the total length of the tract, from the cardia to the rectal end was recorded as the transfer rate, and the results of observation are shown in Table 12. As is seen in Table 12, in the group of rats to which the spherical particles of activated carbon according to the invention were administered, the transfer rate is larger than in the Comparative group, showing the reduced effect of causing constipation.

TABLE 12

| | Intratestinal Transfer Rate of Specimen | | |
|---|---|---|---|
| Property | Specimen According to the Invention | Comparative Specimen (powdery charcoal) | Comparative Specimen (granulated particle) |
| Transfer rate | 72.0 | 52.1 | 54.5 |

Example 8

(Preparation of Particles of Activated Carbon)

The ratio of the diameter of the largest particle to that of the smallest particles was adjusted to 1 to 3 by sifting the spherical particles of activated carbon produced by the same method of Example 1, of 0.1 to 1.5 mm in diameter containing truly spherical particles in a high extent.

The properties of the thus obtained spherical particles of activated carbon are shown in Table 13, and those of the conventional powder of activated carbon and the granulated particle of activated carbon produced by the following method are also shown in Table 13 for comparison as Comparative specimens.

A gel-like precipitate was obtained by mixing the 1 molar aqueous solution of sodium metasilicate into the 1 molar aqueous solution of sodium metasilicate into the 1 molar aqueous solution of sodium aluminate at a temperature of about 50° C. After separating the thus obtained precipitate by centrifugation and washing well with water, the precipitate was added to a 2 molar aqueous solution of magnesium chloride and well mixed. After separating the precipitate, the treatment with magnesium chloride solution was repeated. After separating the thus precipitated product by centrifugation and washing the precipitate with water throughly, a gel-like precipitate aluminum magnesium silicate was obtained.

In the next step, 170 g of powder activated carbon was mixed with 32 g of the above-mentioned gel-like precipitate of aluminum magnesium silicate well suspended in water and the mixture was formulated to granular form under stirring and adjusting tackiness of the mixture by water addition and then dried at a temperature of 60° C. overnight to be granulated carbon.

In Table 13, the adsorbencies of both spherical particles of activated carbon to creatinine is illustrated, creatinine being known as accumulating noxious substances formed in the living body in metabolic abnormality caused by renal diseases.

TABLE 13

| | Specific Properties of Activated Carbon | | |
|---|---|---|---|
| Property | Specimen According to the Invention | Comparative Specimen (powdery charcoal) | Comparative Specimen (granulated particle) |
| Diameter (mm) | 0.26 to 0.6 | 0.6 | 0.1 to 0.6 |
| Specific surface area (m²/g) | 1500 | 950 | 850.0 |
| Pore-volume (ml/g)*1 | 0.35 | 1.8 | 1.7 |
| Adsorbency to creatinine (mg/g)*2 | 63 | 45 | 38 |
| pH*3 | 7.2 | — | — |

Notes
*1 Pore-volume of pores having radius of 100 to 75,000Å, determined by "Porosimetro Model 70" made by Carlo Erba.
*2 Adsorbency was determined in a phosphate buffer solution containing substrate at a concentration of 5 mg/dl at pH of 7.4.
*3 pH of the specimen was determined by the method described in Pharmacopeia Japonica IX Ed. for "charcoal for pharmacological use," that after immersing 3 g of the specimen in 60 ml of distilled water and keeping for 5 minutes in boiling, an amount of distilled water was added to compensate the loss due to evaporation, and the pH of the liquid phase was determined after filtration. The value of the thus determined pH of the liquid phase was taken as the pH of the specimen to be shown in Table 13.

The results of determination on the adsorbencies of the above-mentioned specimens to various digestive enzymes in vitro are shown in Table 14 for reference. In addition, the adsorbency of a commercial powdery charcoal to the same digestive enzymes are also shown in Table 14. The values in Table 14 are the determined value expressed by mg/g obtained by determination on each enzyme as a substrate at a concentration of 1 ml/dl in a phosphate buffer solution at pH of 7.4.

TABLE 14

| | Adsorbencies to Digestive Enzymes | |
|---|---|---|
| Enzyme | Specimen According to the Invention | Powdery Charcoal |
| Pepsin | 8 | 85 |
| Chymotrypsin | 8 | 65 |
| Amylase | smaller than 1 | 5 |
| Lipase | 5 | 35 |

It is recognizable from Table 14 that the adsorbency of the spherical particles of activated carbon according to the invention is generally lower than those of powdery charcoal and of granulated particle to the digestive enzymes.

Example 9

(Adsorbency of the Activated Carbon)

In order to observe the adsorbency of the spherical particles of activated carbon according to the invention, the following experiments were carried out in the presence of sodium stearate which is known to inhibit the adsorption in the intestines of noxious substances by activated carbon.

Into a phosphoric acid-buffer solution at pH of 7.4, sodium stearate was dispersed at a concentration of 2% by weight corresponding to the roughly estimated intestinal concentration of sodium stearate, and further, creatinine was dissolved into the solution at a concentration of 15 mg/dl.

Each of the specimen shown in Table 8 was added to the thus prepared solution and after a 3-hour-shaking, the mixture was divided into portions of 5 ml.

After adding 3 drops of an aqueous 10% by weight aluminum sulfate solution to each aliquot of 5 ml to precipitate stearic acid, the concentration of creatinine in the supernatant layer of the aliquot was determined colorimetrically. The above-mentioned procedures were carried out at a temperature of 37° C. except for the colorimetrical determination. From the values, the minimum concentration of creatinine on each series was obtained to calculate the adsorbed amount of creatinine onto the specimen. The results are shown in Table 15.

As is clearly seen in Table 15, the spherical particles of activated carbon according to the invention are superior to comparative specimens in adsorbency of creatinine. From the result, it its recognizable that the spherical particles of activated carbon according to the invention, even in the presence of a substance such as sodium stearate which inhibits the adsorption of noxious substances such as creatinine by the activated carbon within the intestinal tracts, exhibits an excellent adsorbency of noxious substances such as creatinine.

TABLE 15

| | Adsorbency to Creatinine in the Presence of Sodium Stearate | | |
|---|---|---|---|
| Property | Specimen According to the Invention | Comparative Specimen (powdery charcoal) | Comparative Specimen (granulated particle) |
| Amount of adsorbed creatinine* | 7.8 | 5.6 | 5.0 |

Notes
*Adsorbed amount of creatinine (mg) onto unit amount (g) of specimen of activated carbon.

Example 10

(Function of the Activated Carbon within the Living Body)

An aqueous solution of pentobarbital sodium was orally administered to groups of female Wistar rats of individual body weight of 130 to 140 g at a dose rate of 20 mg of the medicine per kg body weight, and immediately after, an aqueous suspension of each specimen shown in Table 13 was orally administered at a dose rate of 200 mg/kg body weight. A group of the rats was kept as the control by administering only pentobarbital sodium. The number of rats in a group was 10. After pre-determined time periods, blood specimens were collected and the concentrations of pentobarbital sodium in the blood specimen were determined to find the mean value of the maximum concentration of the medicine in the blood. The percentage of the mean of maximum concentrations of the treated group to the mean of maximum concentrations of the control group is shown in Table 16 as the rate of removal of pentobarbital sodium from the rats.

As is seen in Table 16, the effect of removal of the medicine (referred to the effect of detoxication) was observed on every specimen of activated carbon, however, the specimen according to the invention showed a particularly remarkable detoxifying effect as compared to comparative specimens.

TABLE 16

Rate of Removal of Pentobarbital Sodium by Specimens

| Property | Specimen According to the Invention | Comparative Specimen (powdery charcoal) | Comparative Specimen (granulated particle) |
| --- | --- | --- | --- |
| Rate of removal | 98.5 | 89.9 | 79.8 |

After 90 minutes of the administration of each specimen, all the animals were sacrificed by anesthesia and their digestive tracts were removed to observe the intestinal transfer of the administered activated carbon. The ratio (percentage) of the distance from the cardia to the point at which the activated carbon have arrived to the total length of the tract, form the cardia to the rectal end was recorded as the transfer rate, and the results of observation are shown in Table 17. As is seen in Table 17, in the group of rats to which the spherical particles of activated carbon according to the invention were administered, the transfer rate is larger than in the Comparative group, showing the reduced effect of causing constipation.

TABLE 17

Intestinal Transfer Rate of Specimen

| Property | Specimen According to the Invention | Comparative Specimen (powdery charcoal) | Comparative Specimen (granulated particle) |
| --- | --- | --- | --- |
| Transfer rate | 77.5 | 52.1 | 54.5 |

Example 11

(Adsorbency of the Activated Carbon)

In order to observe the adsorbency of the spherical particles of activated carbon according to the invention, the following experiments were carried out in the presence of sodium stearate which is known to inhibit the adsorption of noxious substances by activated carbon in the intestines.

Into a phosphoric acid-buffer solution at pH of 7.4, sodium stearate was dispersed at a concentration 2% by weight corresponding to the roughly estimated intestinal concentration of sodium stearate, and further, creatinine was dissolved into the solution at a concentration of 15 mg/dl.

Each of the specimen shown in Table 13 was added to the thus prepared solution and after a 3-hour-shaking, the mixture was divided into portions of 5 ml.

After adding 3 drops of an aqueous 10% by weight aluminum sulfate solution to each aliquot of 5 ml to precipitate stearic acid, the concentration of creatinine in the supernatant layer of the aliquot was determined colorimetrically. The above-mentioned procedures were carried out at a temperature of 37° C. except for the colorimetrical determination. From the values, the minimum concentration of creatinine on each series was obtained to calculate the adsorbed amount of creatinine onto the specimen. The results are shown in Table 18.

As is clearly seen in Table 18, the spherical particles of activated carbon according to the invention is superior to comparative specimens in adsorbency to creatinine. From the result, it is recognizable that the spherical particles of activated carbon according to the invention, even in the presence of a substance such as sodium stearate which inhibits the absorption of noxious substances such as creatinine by the activated carbon within the intestinal tracts, exhibits an excellent adsorbency to the noxious substances such as creatinine.

TABLE 18

Adsorbency to Creatinine in the Presence of Sodium Stearate

| Property | Specimen According to the Invention | Comparative Specimen (powdery charcoal) | Comparative Specimen (granulated particle) |
| --- | --- | --- | --- |
| Amount of adsorbed creatinine | 18.0 | 5.6 | 5.0 |

Notes
*Adsorbed amount of creatinine (mg) onto unit amount (g) of specimen of activated carbon.

Example 12

(Clinical Cases)

Two women, 24 years old and 36 years old, who had suffered from habitual constipation and pimples on their faces were given between meals 3 g of the medicinal powdery carbon three times a day. From the third day after the beginning of the administration, the number of pimples were found to be slightly reduced, but the patient's constipation increased and they complained of increased pain during bowel movements.

Then the administration of the medicinal powdery carbon was stopped, and specimen 1 and specimen 3 of the spherical particles of activated carbon in Table 1 of Example 1 were respectively administered to the 24 years old and the 36 years old women, at 3 g and three 3 times a day between meals.

In both cases, the number of pimples was gradually reduced from the fourth day and the pimples disappeared substantially one week after the beginning of the administration. Further, it was reported that symptoms of constipation were also mitigated with the disappearance of the pain.

Example 13

(Clinical Case)

A man, 42 years old, who had suffered from the repeated constipation and diarrhea about once a week was administered between meals 5 g of medicinal powder carbon three times a day. As as result, he complained of an increased pain during bowel movements during the period of the constipation. The use of the powdery carbon was stopped and 5 g of the spherical particles of activated carbon of specimen 2 indicated in Table 1 of Example 1 was then administered three times a day between meals. One week after the beginning of administration, he had regular bowel movements with no pain and the symptom of diarrhoea substantially disappeared.

Example 14

(Clinical Case)

In this case, the subject is a male of 59 years old showing acute hepatic symptoms and the impediment of consciousness with a results of normo test of less than 10% and at stage IV of coma. A composition consisting of 100 g of the spherical particles of the activated carbon of specimen 2 in Table 1 of Example 1, 30 g of magnesium hydroxide and 60 ml of syrup of lactulose was divided into 6 portions and the injection of the portions was begun by a naso-oral tube. No aggravation of the patient's conditions was observed in the course of injection.

On the next day, a blood exchange transfusion of 4,000 ml was carried out and the administration of a mixture consisting of the spherical particles of activated carbon/magnesium hydroxide/syrup of lactulose was continued with the result that the improvement in EEG was recognized after three days of illness. Thereafter a daily dose of 50 g of the spherical particles of activated carbon, 30 g of magnesium hydroxide and 30 ml of syrup of lactulose divided into 6 portions was administered. After five days of illness, the man was found to be clearly improved in consciousness, now being able to talk. The normo test was improved remarkably to a level of 32% after seven days of illness and no symptoms of constipation were observed.

Example 15

(Clinical Case)

A man of 48 years of age was hospitalized with conspicuous spider nevus on the whole upper half of his body due to the liver cirrhosis. A treatment of oral administration of the antidote, Sample No. 1-1 of Example 2, was begun at a dose of 5 g/day. After three weeks of the continued administration, his ascites, which had been lightly recognized, disappeared with the increase of urinary output. Then, after 4 to 5 hospital weeks, the spider nevus disappeared conspicuously and he was released from the hospital and went back to his normal daily work.

Example 16

(Clinical Case)

A man of 30 years of age was hospitalized with acute hepatitis showing conspicuously high values of GOT of 490 (Karmen units), of GPT of 830 (Karmen units) and of icteric index of 70. He was treated with the ordinary pharmaceuticals, however, after 2 to 3 hospital weeks, the high values of GOT of 170 to 200, of GPT of 210 to 400 and of icteric index of 100 still continued with a tendency of delayed improvement. After one week of the oral administration of the antidote of the invention, Sample No. 1-1 of Example 2, at a dose of 5 g/day, an improvement was recognized, and after 2 weeks of administration, the values of GOT, GPT and icteric index were reduced to 2, 14, and 35, respectively.

What is claimed is:

1. A method of treating activated carbon, which consists of essentially spherical activated carbon comprising at least 85% in number of microscopically spherical particles of activated carbon which have smooth and convex-curved surface without conspicuous edges and a ratio of the maximum diameter to the minimum diameter of 1.0 to 1.3, said essentially spherical particles of activated carbon being 0.05 to 2 mm in diameter, 500 to 2,000 $m^2/g$ in surface area and 0.05 to 1.0 cc/g in volume of pore cavity determined in the range of pore-radius of 100 to 75,000 Å, to provide an antidotally effective pharmaceutical composition, which comprises contacting said activated carbon with an aqueous ammonia solution, having a $NH_3$ concentration of 1 to 1,000 ppm, to provide the resultant activated carbon having a pH value of 6 to 8.

2. The method of claim 1, in which said essentially spherical particles of activated carbon comprise at least 90% in number of said microscopically spherical particles of activated carbon.

3. The method of claim 1, in which said essentially spherical particles of activated carbon have a particle size in diameter of 0.1 to 1.0 mm.

4. The method of claim 1, in which said essentially spherical particles of activated carbon have a surface area of 700 to 1,500 $m^2/g$.

5. The method of claim 1, in which said essentially spherical particles of activated carbon have a volume of pore cavity of 0.1 to 0.8 cc/g as determined in the range of pore-radius of 100 to 75,000 Å.

6. The method of claim 1, in which the resultant activated carbon has a pH value of 6-7.

7. The method of claim 6, in which the aqueous ammonia solution has a $NH_3$ concentration of 5-100 ppm.

8. The method of claim 6, in which the volume ratio of the aqueous ammonia solution to the particles of activated carbon is 1 to 50.

9. The method of claim 7, in which the volume ratio of the aqueous ammonia solution to the particles of activated carbon is 1 to 50.

10. The method of claim 1, in which the volume ratio of the aqueous ammonia solution to the particles of activated carbon is 1 to 50.

11. The method of claim 1, in which the volume ratio of the aqueous ammonia solution to the particles of activated carbon is 2 to 10.

12. The method of claim 1, in which the volume ratio of the aqueous ammonia solution to the particles of activated carbon is 1 to 50.

13. The method of claim 1, in which the activated carbon is immersed in the aqueous ammonia solution for a time of 0.5-5 hours.

* * * * *

UNITED STATES PATENT AND TRADEMARK OFFICE
CERTIFICATE OF CORRECTION

PATENT NO. : 4,822,765
DATED : April 18, 1989
INVENTOR(S) : Yasushi NISHIMURA

It is certified that error appears in the above-identified patent and that said Letters Patent is hereby corrected as shown below:

Col. 6, line 16, change "pre volume of pores 100-75,000" to --pore volume of pores 100-75,000Å--.

Col. 7, lines 30-31, change "GHO-17" to --GH-17--.

Col. 8, line 32, change "metabolish" to --metabolism--.

Col. 9, line 17, change "name" to --named--.

Col. 9, line 22, change "ureic" to --uric--.

Col. 16, line 17, change "it its" to --it is--.

Col. 15, Table 13, the line of "diameter (mm)" and column of "Comparative Specimen (powdery charcoal)", change "0.6" to --<0.06--.

Signed and Sealed this

Seventeenth Day of April, 1990

Attest:

HARRY F. MANBECK, JR.

*Attesting Officer*      *Commissioner of Patents and Trademarks*